United States Patent [19]

Kishita et al.

[11] Patent Number: 5,117,026
[45] Date of Patent: May 26, 1992

[54] FLUORINE-CONTAINING ORGANIC SILICON COMPOUNDS

[75] Inventors: Hirofumi Kishita, Annaka; Kouichi Yamaguchi, Takasaki; Hideki Fujii, Annaka; Shuji Suganuma, Takasaki; Yoshikazu Saito, Annaka; Shinichi Sato, Annaka; Kenichi Fukuda, Annaka; Nobuyuki Kobayashi, Annaka, all of Japan

[73] Assignee: Shin-Etsu Chemical Co., Ltd., Tokyo, Japan

[21] Appl. No.: 723,980

[22] Filed: Jul. 1, 1991

[30] Foreign Application Priority Data

Jun. 29, 1990 [JP] Japan .................. 2-171563
Jun. 29, 1990 [JP] Japan .................. 2-171565

[51] Int. Cl.$^5$ .............................................. C07F 7/08
[52] U.S. Cl. .................................................. 556/435
[58] Field of Search ......................................... 556/435

[56] References Cited

U.S. PATENT DOCUMENTS 3,527,781  9/1970  Levin ................. 556/435 X
3,647,740  3/1972  Loree et al. .......... 556/435 X Primary Examiner—Paul F. Shaver
Attorney, Agent, or Firm—Oblon, Spivak, McClelland, Maier & Neustadt

[57] ABSTRACT

The synthesis and use of a fluorine-containing organic silicon compound represented by:

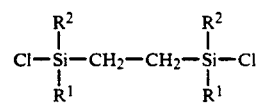

wherein each $R^1$ independently represents a monovalent hydrocarbon group of 1-10 carbon atoms, and each $R^2$ independently represents a monovalent hydrocarbon group of 1-10 carbon atoms or a $CH_2CH_2Rf$ group, such that at least one $R^2$ is $CH_2CH_2Rf$, wherein Rf is a perfluoroalkyl group of 1-10 carbon atoms; the compounds of formula (I) are useful in the preparation of fluorine-containing polysilethylenesiloxanes having excellent solvent-resisting and surface-lubricating properties.

13 Claims, 3 Drawing Sheets

FLUORINE-CONTAINING ORGANIC SILICON COMPOUNDS

BACKGROUND OF THE INVENTION

The present invention relates to novel fluorine-containing organic silicon compounds.

It is known that a polysiloxane containing fluorine atom(s) in the molecule is useful as a material to produce a rubber having excellent solvent resisting and chemical resisting characteristics, as well as as surface-lubricating and water- and oil-repelling agents. A need continues to exist, however, for polysiloxane compounds which exhibit improvements in these properties.

In the course of conducting research to meet this goal, the present Inventors have discovered novel fluorine-containing organic silicon compounds, useful as a starting material in the production of fluorine-containing polysiloxanes.

SUMMARY OF THE INVENTION

Therefore, it is an object of the invention to provide novel fluorine-containing organic silicon compounds useful as a starting material for production of fluorine-containing polysiloxanes.

A further object of the present invention is to provide a method for manufacturing novel fluorine-containing organic silicon compounds.

A further object of the present invention is to provide novel fluorine-containing organic silicon compounds useful for the production of fluorine-containing polysiloxanes having improved solvent resisting and chemical resisting properties.

A further object of the present invention is to provide novel fluorine-containing organic silicon compounds useful for the production of fluorine-containing polysiloxanes exhibiting improved water-repelling and oil-repelling properties.

A further object of the present invention is to provide novel fluorine-containing organic silicon compounds useful for the production of fluorine-containing polysiloxanes exhibiting improved surface-lubricating properties.

These and other objects, which will become apparent during the following detailed description of the present invention, have been achieved by the present Inventors' discovery that novel fluorine-containing organic silicon compound represented by the following formula (I):

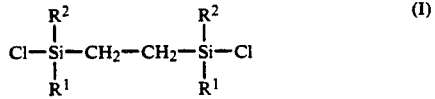

wherein each $R^1$ independently represents a monovalent hydrocarbon group of 1–10 carbon atoms, and each $R^2$ independently represents a monovalent hydrocarbon group of 1–10 carbon atoms or a $CH_2CH_2Rf$ group, such that at least one $R^2$ is $CH_2CH_2Rf$, wherein Rf is a perfluoroalkyl group of 1–10 carbon atoms, are useful as a starting material for production of fluorine-containing polysiloxanes exhibiting improved chemical-resisting and surface-lubricating characteristics.

The present invention can be broken down into two groups of compounds, one group being represented by the following formula (II):

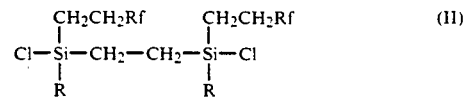

wherein each R independently represents monovalent hydrocarbon groups of 1–10 carbon atoms, and Rf is the same as above, and the other group being represented by the following formula (III):

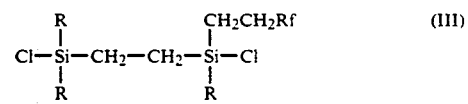

wherein R and Rf are defined as above.

DETAILED DESCRIPTION OF THE PREFERRED EMBODIMENTS

1. Manufacture of Fluorine-Containing Organic Silicon Compounds

The fluorine-containing organic silicon compounds of the present invention represented by formula (II) are produced by an addition reaction between a hydrosilane represented by the following formula (IV):

and a vinyl silane represented by the following formula (V):

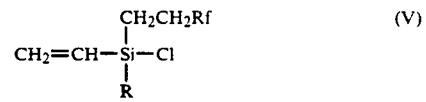

wherein each R and Rf is as defined in the formula (II), in the presence of a catalyst.

Preferred examples of the perfluoroalkyl group Rf of 1–10 carbon atoms include: $-CF_3$, $-C_4F_9$, $-C_6F_{13}$, $-C_8F_{17}$.

Examples of the monovalent hydrocarbon of 1–10 carbon atoms represented by R include straight-chain or branched alkyls such as such as methyl, ethyl, propyl, butyl, pentyl, hexyl, heptyl, octyl, nonyl, decyl, isobutyl, t-butyl, isopentyl, neopentyl, t-hexyl, and isooctyl; cycloalkyls such as cyclohexyl, cyclobutyl, cyclopentyl, cyclohexyl, cyclooctyl and cyclodecyl; straight-chain or branched alkenyls such as vinyl, allyl, methallyl, 2-propenyl, butenyl pentenyl, hexenyl, octenyl, decenyl, and isoprenyl (3-methyl-2-bytenyl); alkynyls such as ethynyl, propynyl, propargyl, butynyl, pentynyl, hexynyl, octynyl, and decynyl; aryls such as phenyl, tolyl, xylyl, ethylphenyl, cumyl, isopropylphenyl, t-butylphenyl and α- and β-naphtyl; and aralkyls such as benzyl, 2-phenylethyl. In the present invention, alkyls of 1–10 carbon atoms are preferred, lower alkyls (of 1–4 carbon atoms) are more preferred and methyl is the most preferred.

The more effective catalysts to facilitate the addition reaction between hydrosilane and vinyl silane are ones that contain a platinum group metal. Examples are chloroplatinic acid; alcohol-modified chloroplatinic acid (for example, those disclosed in U.S. Pat. No. 3,220,972, which are incorporated herein by reference); a complex formed from chloroplatinic acid and olefin (for example, those disclosed in U.S. Pat. Nos. 3,159,601; 3,159,662; 3,775,452); platinum black or palladium supported on a support such as alumina, silica and carbon; and rhodium-olefin complex. Among these catalysts, those of the complex type (for example, those binding an olefin ($\pi$-complex) or an alcohol, amine or phosphine ($\sigma$-complex)) perform better when dissolved in certain solvents such as an alcohol, ketone, ether and/or hydrocarbon. The amount of the platinum group metal-containing catalyst is such that the net weight of the platinum group metal is 0.1–500 ppm, more preferably 0.5–200 ppm, of the combined weight of the hydrosilane and vinyl silane.

The reaction between the hydrosilane and the vinyl silane can be conducted in a solventless system. If necessary or desired, however, the reaction can be effected in an inactive solvent such as toluene, xylene, benzene, n-hexane, n-heptane, cyclohexane, or any mixture thereof. Preferably, the reaction temperature is 60°–150° C., more preferably 70°–135° C., and most preferably, 80°–120° C.

When the reaction is complete, the product is refined by a known refinery process such as distillation or crystallization, distillation being the preferred process, and the desired fluorine-containing organic silicon compound is obtained.

The present fluorine-containing organic silicon compounds obtained in this manner are found to have the molecular structure of the general formula (II). Some of the typical examples of the first group of the inventive fluorine-containing organic silicon compounds of the present invention are as follows:

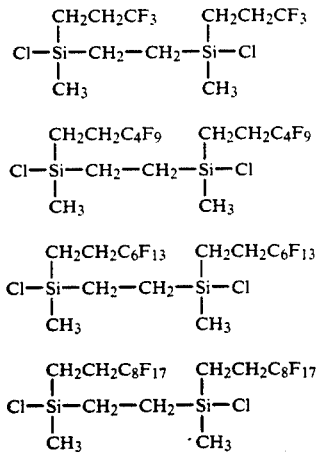

The fluorine-containing organic silicon compounds of the present invention represented by formula (III) are produced by an addition reaction between a hydrosilane represented by the following formula (VI):

$$\begin{array}{c} R \\ | \\ H-Si-Cl \\ | \\ R \end{array} \quad (VI)$$

and a vinyl silane represented by the following formula (VII):

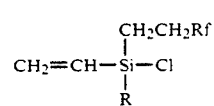

$$\begin{array}{c} CH_2CH_2Rf \\ | \\ CH_2=CH-Si-Cl \\ | \\ R \end{array} \quad (VII)$$

wherein each R and Rf are defined as in the formula (III), in the presence of a catalyst.

Representative examples of R and Rf groups are the same as those enumerated above for the compounds of the formulas (I)–(V).

The vinyl silane represented by the formula (VII) can be synthesized, for example, through a reaction between a vinyl Grignard reagent such as vinyl magnesium bromide and a dichlorosilane having a perfluoroalkylethyl group.

The preferred examples and suitable amounts of the catalyst for the addition reaction between the hydrosilane of the formula (VI) and the vinyl silane of the formula (VII) are the same as those recommended above for the addition reaction between the hydrosilane of the formula (IV) and the vinyl silane of the formula (V).

Similar to the addition reaction between the hydrosilane of the formula (IV) and the vinyl silane of the formula (V) above, the reaction between the hydrosilane of the formula (VI) and the vinyl silane of the formula (VII) can be conducted in a solventless system. However, if desired or necessary, the reaction can be effected in an inactive solvent such as toluene, xylene, benzene, n-hexane, n-heptane, cyclohexane or any mixture thereof. A preferred temperature for the reaction is 60°–150° C., more preferably 70°–135° C., and most preferably 80°–120° C.

When the reaction is complete, the product is refined by a known process such as distillation or crystallization, distillation being the preferred process, and the desired fluorine-containing organic silicon compound is obtained.

The present fluorine-containing organic silicon compound obtained in this manner was found to have the molecular structure of the general formula (III). Some of the typical examples of the second group of the inventive fluorine-containing organic silicon compound are as follows:

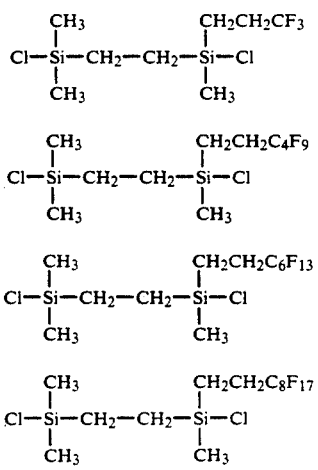

II. Applications of the Fluorine-Containing Organic Silicon Compounds of the Present Invention The present fluorine-containing organic silicon compounds can be used in various applications, but their greatest utility lies in the production of polysilethylenesiloxanes, which have excellent solvent resisting properties. To produce such polysilethylenesiloxanes, the present fluorine-containing organic silicon compounds are hydrolyzed, then cracked in the presence of an alkali metal hydroxide, whereby a 5-membered ring monomer is obtained. The 5-membered ring monomer is polymerized, and thus, polysilethylenesiloxane polymer is synthesized. Having high fluorine content, this polymer is especially useful as a material to manufacture solvent-resistive silethylenesiloxane rubber, surface lubricating agent which renders surfaces nonadherent and highly resistant to oil, water and other chemicals, etc.

Other features of the present invention will become apparent in the course of the following descriptions of examples which are given for illustration of the present invention, and are not intended to be limiting thereof.

EXAMPLES

EXAMPLE 1

A 2-liter four-necked flask equipped with a reflux condenser, a stirrer, a thermometer, and a dropping funnel was charged with 613 g (3.03 mol) of trichloropropylvinylmethylchlorosilane and 0.1 g of a 1% isopropanol solution of chloroplatinic acid. The mixture was heated at 80° C., then 535 g (3.03 mol) of trichloropropylmethylsilane was added dropwise into the flask via the dropping funnel over the course of 2 hours.

Afterwards, the mixture was stirred and heated at 80° C. for one hour. The reaction mixture was then distilled under a reduced pressure, and 1017 g (89% yield) of a fraction having a boiling point of 102°–103° C. (3 mmHg) and a melting point of 39° C. was obtained. The fraction was analyzed by $^1$H-NMR spectroscopy, infrared (IR) absorption spectroscopy, $^{19}$F-NMR spectroscopy, and elemental analysis, and the results are as follows.

$^1$H-NMR spectrum (in CCl$_4$, internal standard CHCl$_3$): δ (ppm) 0.50 (s, Si—CH$_3$, 6H) 0.88 (s, Si—CH$_2$CH$_2$—Si, 4H) 1.08 (t, Si—CH$_2$, 4H) 2.18 (t, CF$_3$—CH$_2$, 4H)

Figure 1:
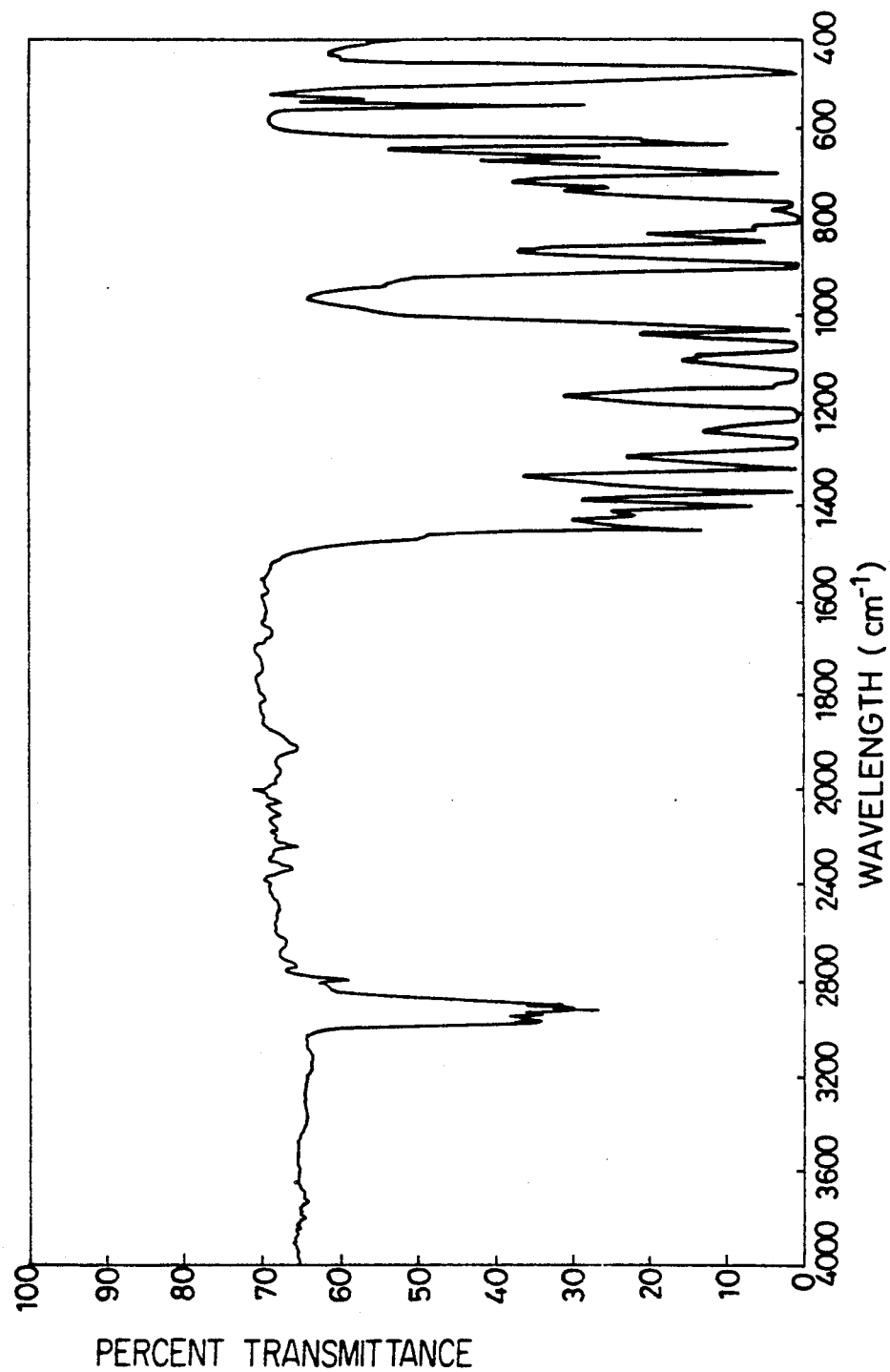
FIG. 1 is an infrared spectrum chart of the compound of Example 1.

IR absorption spectrum (see FIG. 1): 1400–1000 cm$^{-1}$ (C-F)

$^{19}$F-NMR spectrum (CF$_3$COOH standard): −7.0 ppm (CF$_3$)

| Elemental analysis: | C | H | Si | F | O |
|---|---|---|---|---|---|
| Percentage calculated | 31.7 | 4.7 | 14.8 | 30.1 | 18.7 |
| Percentage measured | 31.7 | 4.8 | 14.8 | 30.0 | 18.7 |

From analysis of the above spectra, the fraction was confirmed to be a compound represented by the following formula:

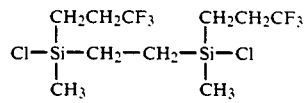

EXAMPLE 2

A 3-liter four-necked flask equipped with a reflux condenser, a stirrer, a thermometer, and a dropping funnel was charged with 823 g (2.34 mol) of a vinylsilane of the following formula

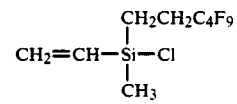

and 0.085 g of a 1% isopropanol solution of chloroplatinic acid. The mixture was heated at 80° C., then 763 g (2.34 mol) of a hydrosilane of the following formula:

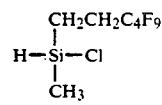

was added dropwise into the flask via the dropping funnel over the course of 2 hours.

Afterwards, the mixture was stirred and heated at 80° C. for one hour. The reaction mixture was then distilled under a reduced pressure, and 1069 g (67% yield) of a fraction having a boiling point of 121°–124° C. (1 mmHg) and a melting point of 39° C. was obtained. The fraction was analyzed by $^1$H-NMR spectroscopy, infrared (IR) absorption spectroscopy, $^{19}$F-NMR spectroscopy, and elemental analysis, and the results are as follows.

$^1$H-NMR spectrum (in CCl$_4$, internal standard CHCl$_3$): δ (ppm) 0.50 (s, Si—CH$_3$, 6H) 0.90 (s, Si—CH$_2$CH$_2$—Si, 4H) 1.07 (t, Si—CH$_2$, 4H) 2.13 (t, CF$_2$—CH$_2$, 4H)

Figure 2:
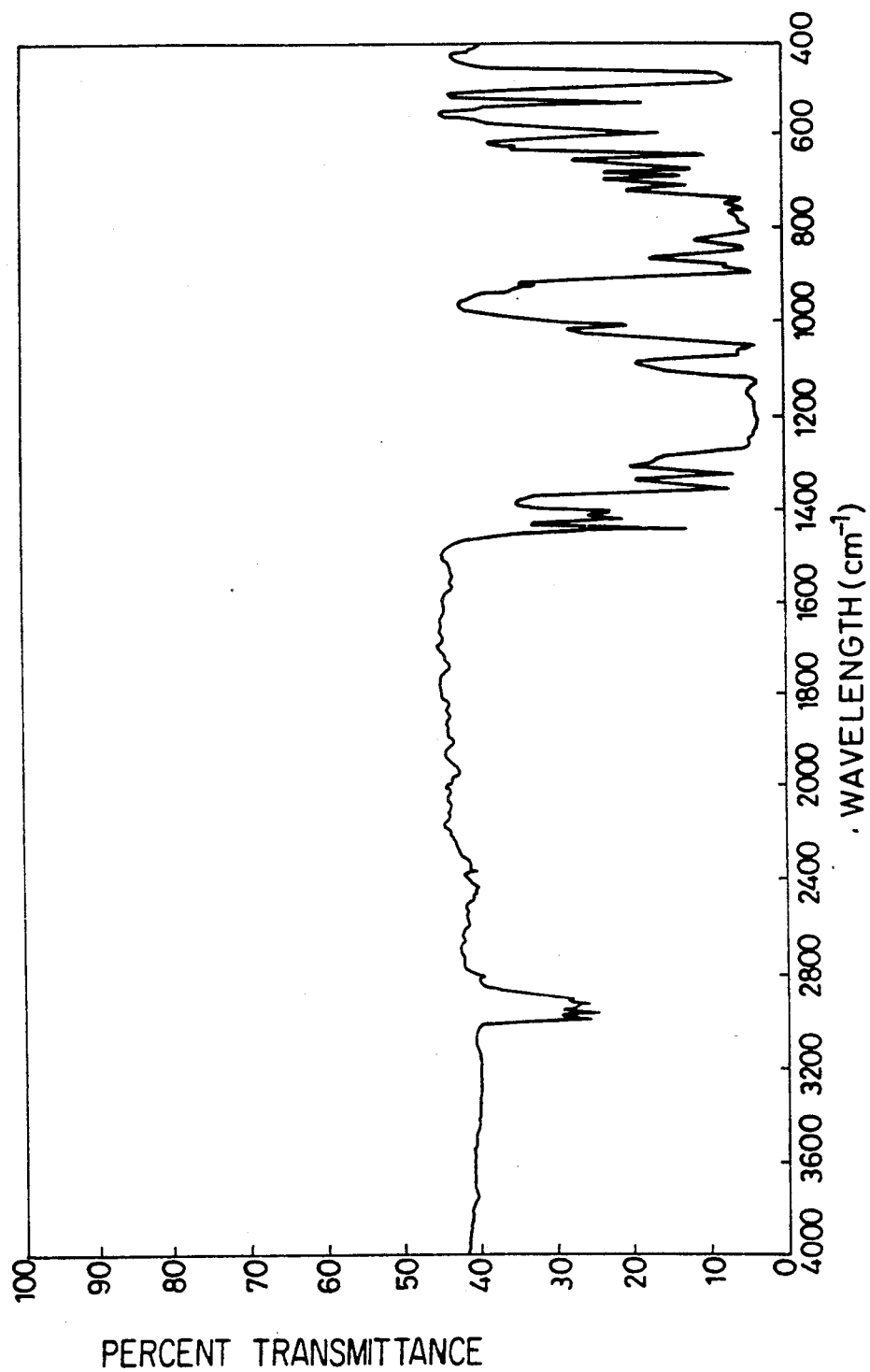
FIG. 2 is an infrared spectrum chart of the compound of Example 2.

IR absorption spectrum (see FIG. 2): 1000–1400 cm$^{-1}$ (C-F)

$^{19}$F-NMR spectrum (CF$_3$COOH standard):

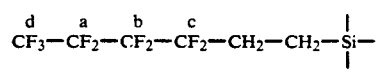

a: −51.20 ppm
b: −49.37 ppm
c: −41.17 ppm
d: −6.92 ppm

| Elemental analysis: | C | H | Si | F | O |
|---|---|---|---|---|---|
| Percentage calculated | 28.3 | 2.7 | 8.2 | 50.4 | 10.4 |
| Percentage measured | 28.2 | 2.7 | 8.3 | 50.2 | 10.5 |

From analysis of the above spectra, the fraction was confirmed to be a compound represented by the following formula:

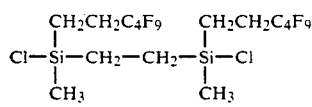

EXAMPLE 3

Synthesis of heptadecaphlorodecylvinylmethylchlorosilane:

A 10-liter four-necked flask equipped with a reflux condenser, a stirrer, a thermometer, and a dropping funnel was charged with 2525 g of heptadecaphlorodecylvinylmethylchlorosilane and 2500 g of tetrahydrofuran. Then, 2489 g of a tetrahydrofuran solution of vinylmagnesium bromide (4.5 mol of vinylmagnesium bromide), which had been prepared in advance, was was added dropwise into the flask via the dropping funnel over the course of 2 hours.

Afterwards, the mixture was stirred and heated at 60° C. for three hours. The reaction mixture was analyzed by gas chromatography, and a peak attributable to the starting material heptadecaphlorodecylmethyldichlorosilane (A) and a peak attributable to a mixture of both the desired product heptadecaphlorodecylvinylmethylchlorosilane (B) and the side product heptadecaphlorodecyldivinylmethylsilane (C) were observed in respective percentages of 8.6% and 11.8%.

The reaction mixture was filtered by suction, and the salt was removed. The filtrate was distilled under a reduced pressure, and 1819 g of a fraction (A=32.3%, B+C=66.2%) having a boiling point of 105°-110° C. (7 mmHg) was obtained.

Synthesis of 2-(dimethylchlorosilyl)ethylheptadecafluorooctylmethylchlorosilane:

A 3-liter four-necked flask equipped with a reflux condenser, a stirrer, a thermometer, and a dropping funnel was charged with 1527 g of the fraction obtained in the abovedescribed preparation and 0.1 g of a 1% isopropanol solution of chloroplatinic acid. The mixture was heated at 80° C., then 261 g of dimethylchlorosilane was added dropwise into the flask via the dropping funnel over the course of 2 hours.

Afterwards, the mixture was stirred and heated at 80° C. for one hour. The reaction mixture was distilled under a reduced pressure, and 515 g (72.0% yield based on the amount of heptadecafluorooctylvinylmethylchlorosilane) of a fraction having a boiling point of 158°-160° C. (8 mmHg) and a melting point of 38°-40° C. was obtained. The fraction was analyzed by $^1$H-NMR spectroscopy, IR absorption spectroscopy, $^{19}$F-NMR spectroscopy, and elemental analysis, and the results are as follows.

$^1$H-NMR spectrum (in CCl$_4$, internal standard CHCl$_3$): δ (ppm)

0.55 (s, Si—CH$_3$, 6H)
0.57 (s, Si—CH$_3$, 3H)
1.01 (s, Si—CH$_2$CH$_2$—Si, 4H)
1.22 (t, Si—CH$_2$, 2H)
2.36 (t, CF$_2$—CH$_2$, 2H)

Figure 3:
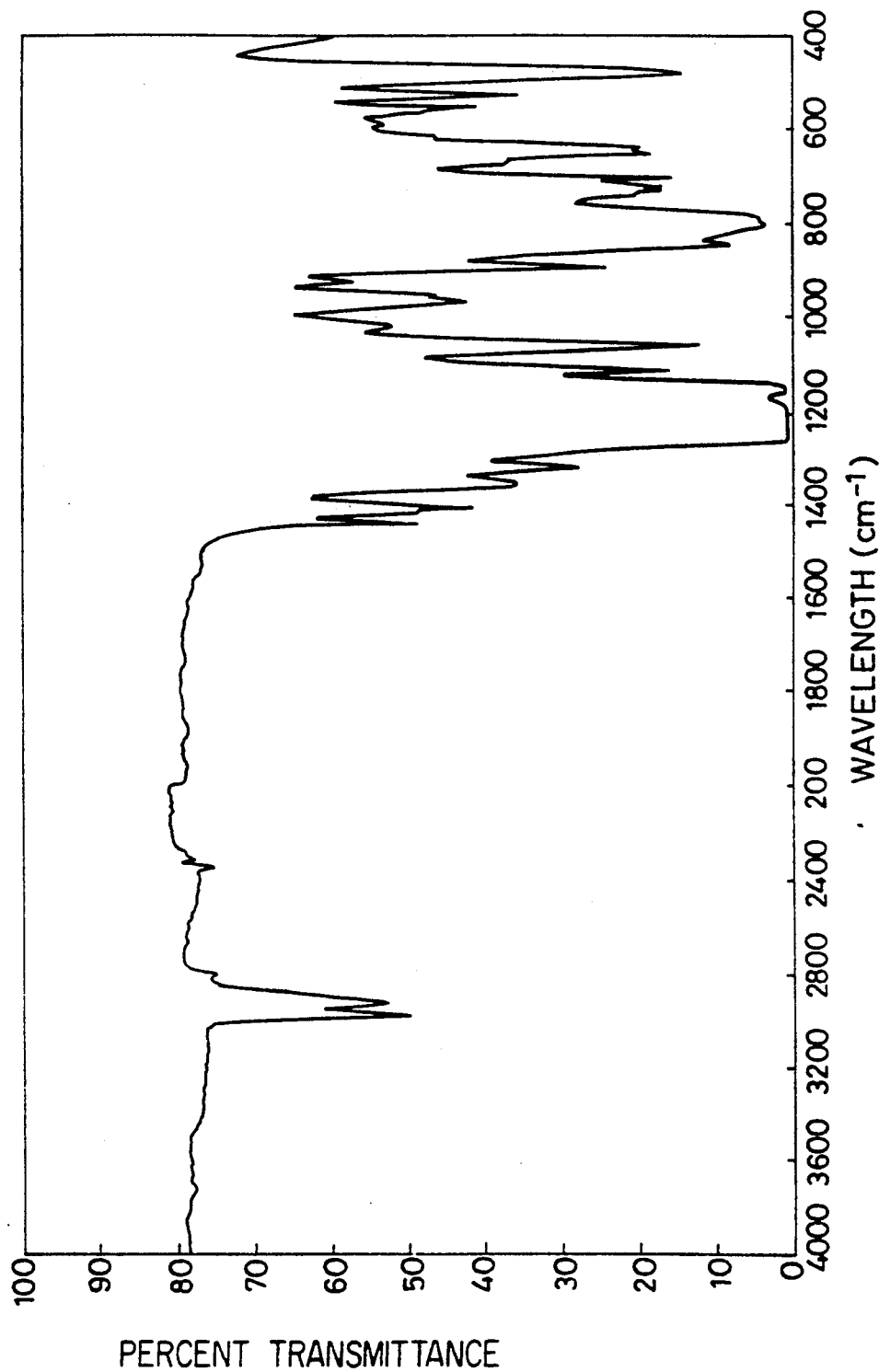
FIG. 3 is an infrared spectrum chart of the compound of Example 3.

IR absorption spectrum (see FIG. 3): 1280-1130 cm$^{-1}$ (C-F)

$^{19}$F-NMR spectrum (CF$_3$COOH standard):

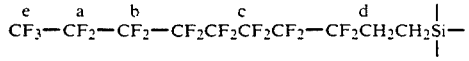

a: −50.55 ppm
b: −47.25 ppm
c: −46.15 ppm
d: −40.15 ppm
e: −5.71 ppm

| Elemental analysis: | C | H | Si | F | Cl |
|---|---|---|---|---|---|
| Percentage calculated | 27.8 | 2.7 | 8.7 | 49.9 | 11.0 |
| Percentage measured | 27.9 | 2.5 | 8.8 | 50.0 | 10.8 |

From analysis of the above spectra, the fraction was confirmed to be a compound represented by the following formula:

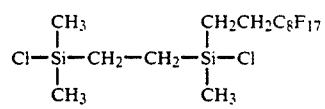

Obviously, numerous modifications and variation of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A fluorine-containing organic silicon compound represented by:

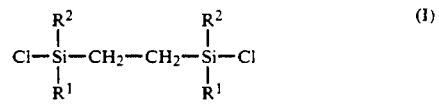

wherein each R$^1$ independently represents a monovalent hydrocarbon group of 1-10 carbon atoms, and each R$^2$ independently represents a monovalent hydrocarbon group of 1-10 carbon atoms or a CH$_2$CH$_2$Rf group, such that at least one R$^2$ is CH$_2$CH$_2$Rf, wherein Rf is a perfluoroalkyl group of 1-10 carbon atoms.

2. The fluorine-containing organic silicon compound as claimed in claim 1, wherein each of R$^2$ is CH$_2$CH$_2$Rf.

3. The fluorine-containing organic silicon compound as claimed in claim 1, wherein one R$^2$ is CH$_2$CH$_2$Rf.

4. A method of manufacturing the compound of claim 2, comprising reacting a hydrosilane represented by the formula

and a vinyl silane represented by the formula

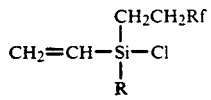

(V)

wherein each R independently represents a monovalent hydrocarbon group of 1-10 carbon atoms, and Rf is a perfluoroalkyl group of 1-10 carbon atoms, in the presence of a catalyst.

5. A method of manufacturing the compound of claim 3 comprising reacting a hydrosilane represented by the formula

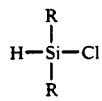

(VI)

and a vinyl silane represented by the formula

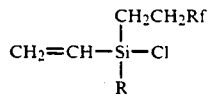

(VII)

wherein each R independently represents a monovalent hydrocarbon groups of 1-10 carbon atoms, and Rf is a perfluoroalkyl group of 1-10 carbon atoms, in the presence of a catalyst.

6. The compound as claimed in claim 2 or 3, wherein R is methyl.

7. The method as claimed in claim 4 or 5, wherein R is methyl.

8. The compound as claimed in claim 2 or 3, wherein Rf is —$CF_3$, —$C_4F_9$, —$C_6F_{13}$, or —$C_8F_{17}$.

9. The method as claimed in claim 4 or 5, wherein Rf is —$CF_3$, —$C_4F_9$, —$C_6F_{13}$, or —$C_8F_{17}$.

10. The compound as claimed in claim 2 or 3, wherein the catalyst is chloroplatinic acid.

11. The method as claimed in claim 4 or 5, wherein the catalyst is chloroplatinic acid.

12. The method as claimed in claim 4 or 5, wherein the reaction temperature is 60°-150° C,.

13. The method as claimed in claim 12, wherein the reaction temperature is 80°-120° C.

* * * * *